United States Patent [19]

Adachi et al.

[11] Patent Number: 4,579,685

[45] Date of Patent: Apr. 1, 1986

[54] PROCESS FOR PREPARING 1-SUBSTITUTED-1,4-BENZODIAZEPINE DERIVATIVES

[75] Inventors: Makoto Adachi; Kazuyuki Sasakura, both of Nara; Tsutomu Sugasawa, Hyogo, all of Japan

[73] Assignee: Shionogi & Co., Ltd., Osaka, Japan

[21] Appl. No.: 635,128

[22] Filed: Jul. 27, 1984

[30] Foreign Application Priority Data

Aug. 11, 1983 [JP] Japan ................. 58-147860

[51] Int. Cl.[4] ................. C07D 243/28; C07D 211/58; C07D 207/14

[52] U.S. Cl. ................. 260/239.3 D; 546/223; 548/578

[58] Field of Search ................. 260/239.3 D; 546/223; 548/578

[56] References Cited

U.S. PATENT DOCUMENTS 3,641,002  2/1972  Yamamoto et al. ......... 260/239.3 D

FOREIGN PATENT DOCUMENTS 1117061  6/1968  United Kingdom ........ 260/239.3 D
2133008  7/1984  United Kingdom ........ 260/239.3 D

OTHER PUBLICATIONS

Natsugari et al. "Chem Pharm. Bull." vol. 27, No. 9, pp. 2084-2092 (1979).

Primary Examiner—Robert T. Bond
Attorney, Agent, or Firm—Birch, Stewart, Kolasch & Birch

[57] ABSTRACT

Improvement in the production of psychotropic 1-substituted-1,3-dihydro-1,4-benzodiazepin-2-ones starting from 2-(1-substituted)amino-benzophenonimines through novel intermediates of the formula:

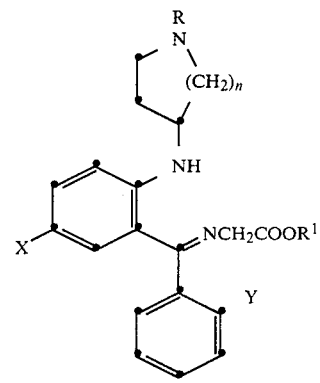

(wherein R is hydrogen, methyl or benzyl, $R^1$ is $C_1$-$C_5$ alkyl or phenyl-$C_1$-$C_5$ alkyl, X and Y each is hydrogen or halogen and n is an integer of 1 to 2)

with economical and industrial advantage.

19 Claims, No Drawings

PROCESS FOR PREPARING 1-SUBSTITUTED-1,4-BENZODIAZEPINE DERIVATIVES

The present invention relates to a process for preparing 1-substituted-1,4-benzodiazepine derivatives. More particularly, this invention is directed to a process for preparing a compound of the formula:

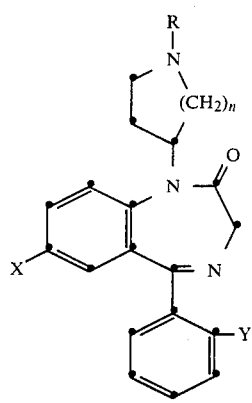

(I)

(wherein R is hydrogen methyl, or benzyl, X and Y each is hydrogen or halogen and n is an integer of 1 to 2)

or its acid addition salts which comprises reacting a compound of the formula:

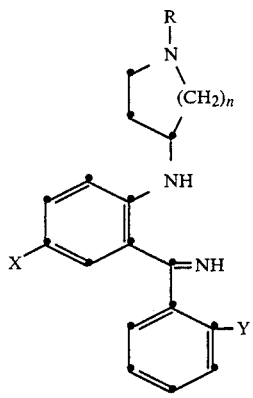

(II)

(wherein R, X, Y and n are as defined above) with a glycine ester to give a compound of the formula:

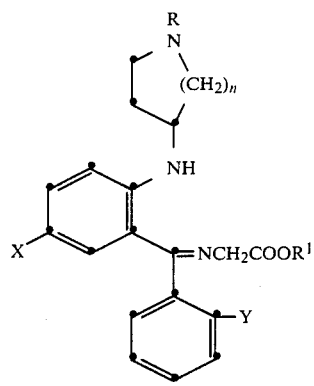

(III)

(wherein $R^1$ is $C_1$–$C_5$ alkyl or phenyl-$C_1$–$C_5$ alkyl and R, X, Y and n are as defined above) and treating the product (III) with an acid.

It has been found by the present inventors that the compounds (I) are useful as psychotropic agents such as antidepressants, antianxiety agents or anticonvulsive agents, but several defects including multi-step synthesis and insufficiency of the yield remained therein in their production [Brit. Unexamd. Pat. Publn. No. 2,133,008]. Moreover, U.S. Pat. No. 3,641,002 discloses the fantom 1-(4-piperidinyl)-1,4-benzodiazepine derivatives without physicochemical data, but the preparation of them seems to be inoperable through the synthetic process disclosed therein. These and other defects on their synthesis have now been overcome by the present inventors.

The wordings in the above definition are explained below:

exemplary $C_1$–$C_5$ alkyl are methyl, ethyl, propyl, isopropyl, butyl, isobutyl, s-butyl, t-butyl, pentyl, and neopentyl, phenyl-$C_1$–$C_5$ alkyl includes benzyl, phenylpropyl and phenylbutyl, and the halogen illustratively includes fluorine, chlorine, bromine and iodine.

The starting materials (II) used in the present invention can be prepared, for example, by reacting a compound of the formula:

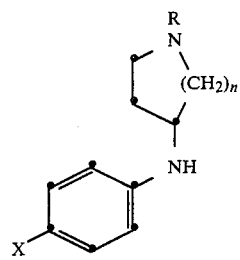

(IV)

(wherein R, X and n are as defined above) with a compound of the formula:

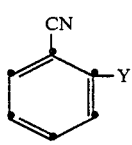

(V)

(wherein Y is as defined above)

in the presence of boron trifluoride and silicon tetrachloride [Brit. Unexamd. Pat. Publn. No. 2,133,008].

The reaction of the starting material (II) with a glycine ester is performed in an appropriate solvent such as methanol, ethanol, dimethylformamide, dimethylsulfoxide chloroform, or the like under heating up to about the boiling point of the solvent. The glycine ester such as glycine alkyl ester (e.g. glycine methyl ester, glycine ethyl ester or glycine propyl ester) or glycine phenyl alkyl ester (e.g. glycine benzyl ester) is preferably used in the form of a mineral acid salt such as hydrochloride, sulfate or the like.

The ring closing reaction of the thus obtained ester (II) is performed by treating with an acid such as acetic acid trifluoroacetic acid, trichloroacetic acid, sulfuric acid, methanesulfonic acid, p-toluene-sulfonic acid or polyphosphoric acid at a temperature of about 20° to 150° C., preferably about 50° to 100° C. The present reaction proceeds in general without a solvent, but may be performed in the presence of an appropriate solvent such as dichloroethane, carbon tetrachloride, chloroform, benzene, toluene or the like if necessary.

Alternatively the compound (Ib, R=hydrogen in the formula I) can be prepared by reacting the compound (Ia, R=methyl or benzyl in the formula I) with an alkyl chloroformate such as methyl chloroformate or ethyl chloroformate in the presence or absence of a base to give once the corresponding carbamate (VI) and subjecting it to the hydrolysis in the presence of an acid.

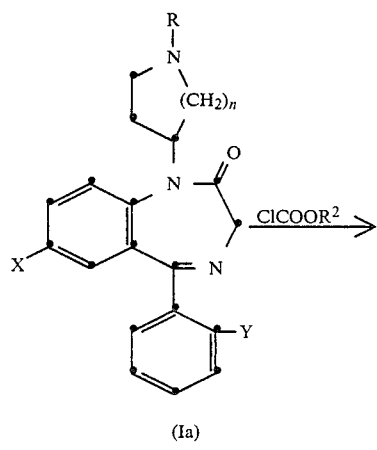

(Ia)

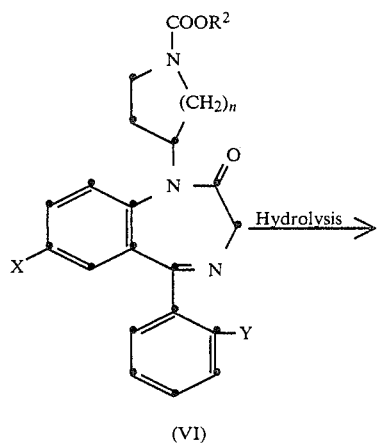

(VI)

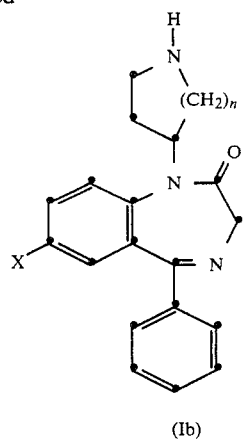

(Ib)

(wherein R is methyl or benzyl, $R^2$ is alkyl or phenylalkyl and X, Y and n are as defined above).

The reaction with $ClCOOR^2$ is performed in the presence of an inorganic base such as alkali carbonate or alkali hydrogencarbonate in an appropriate solvent such as chloroform, carbon tetrachloride, dimethylformamide, dimethylsulfoxide or benzene under heating at a temperature of about 20° to 150° C., preferably 50° to 100° C.

The subsequent hydrolysis is performed by using an appropriate acid such as sulfuric acid, methanesulfonic acid, p-toluenesulfonic acid, polyphosphoric acid, acetic acid or the like in the presence of a sulfide such as tetrahydrothiophene or an alkyl sulfide (e.g. methyl sulfide or ethyl sulfide) under heating at a temperature of about 20° to 150° C., preferably 50° to 100° C.

The dimethylation can be also performed by reating the N-methyl compound (Ia) with 1-chloroethyl chloroformate in an appropriate solvent such as methylene chloride or dichloroethane and then treating with methanol. The reactions may be performed at 30° to 120° C.

Accordingly, the present inventors have succeeded in developing an economical process for preparing the objective 1-substituted-1,4-benzodiazepines (I) by way of the novel intermediary compounds (III).

Practical embodiments of the present invention are illustratively shown in the following examples.

EXAMPLE 1

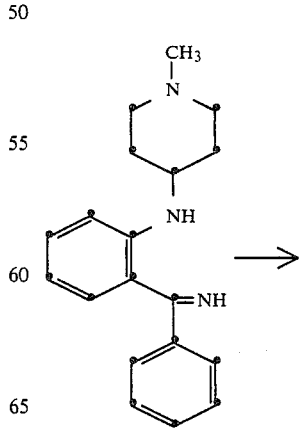

1

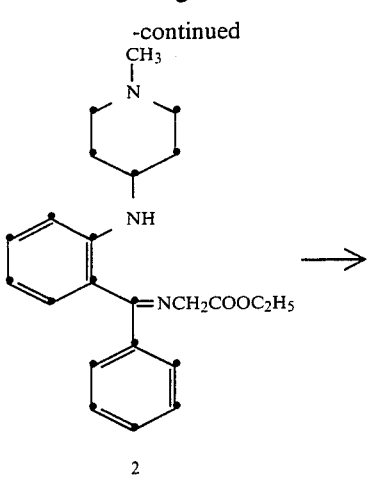

2

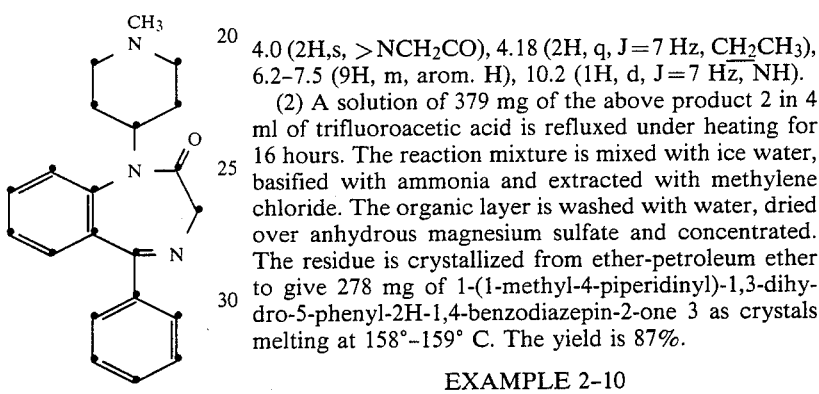

3

(1) A solution of 3 g (10.2 mmol) of 2-(1-methyl-4-piperidinyl)aminobenzophenoneimine 1, 0.59 ml (10.2 mmol) of acetic acid, and 1.57 g (10.2×1.1 mmol) of ethyl glycine hydrochloride in 30 ml of ethanol is refluxed under heating for an hour. After evaporating the solvent, the residue is basified with ammonia and extracted with methylene chloride. The organic layer is washed with water, dried over anhydrous magnesium sulfate and concentrated. The residue is crystallized from ether-petroleum ether to give 2.22 g of ethyl 2-[[[2-(1-methyl-4-piperidinyl)aminophenyl](phenyl)methylen]amino]acetate 2 as crystals melting at 102° to 103° C. The yield is 98%.

IR $\gamma_{max}^{CHCl_3}$: 3180 (NH), 1746 (COOC$_2$H$_5$) cm$^{-1}$.

$^1$HNMR: $\delta^{CDCl_3}$: 1.23 (3H, t, J=7 Hz, CH$_2$CH$_3$), 1.6-3.0 (8H, m aliph. H), 2.3 (3H,s, NCH$_3$), 3.45

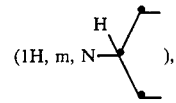

4.0 (2H,s, >NCH$_2$CO), 4.18 (2H, q, J=7 Hz, CH$_2$CH$_3$), 6.2-7.5 (9H, m, arom. H), 10.2 (1H, d, J=7 Hz, NH).

(2) A solution of 379 mg of the above product 2 in 4 ml of trifluoroacetic acid is refluxed under heating for 16 hours. The reaction mixture is mixed with ice water, basified with ammonia and extracted with methylene chloride. The organic layer is washed with water, dried over anhydrous magnesium sulfate and concentrated. The residue is crystallized from ether-petroleum ether to give 278 mg of 1-(1-methyl-4-piperidinyl)-1,3-dihydro-5-phenyl-2H-1,4-benzodiazepin-2-one 3 as crystals melting at 158°-159° C. The yield is 87%.

EXAMPLE 2-10

The reactions are performed as in Example 1, using the following starting materials (II), whereby the corresponding objective compound (I) is prepared by way of the intermediate (IIIa).

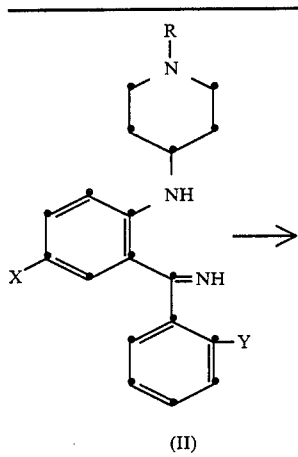

(II)

-continued

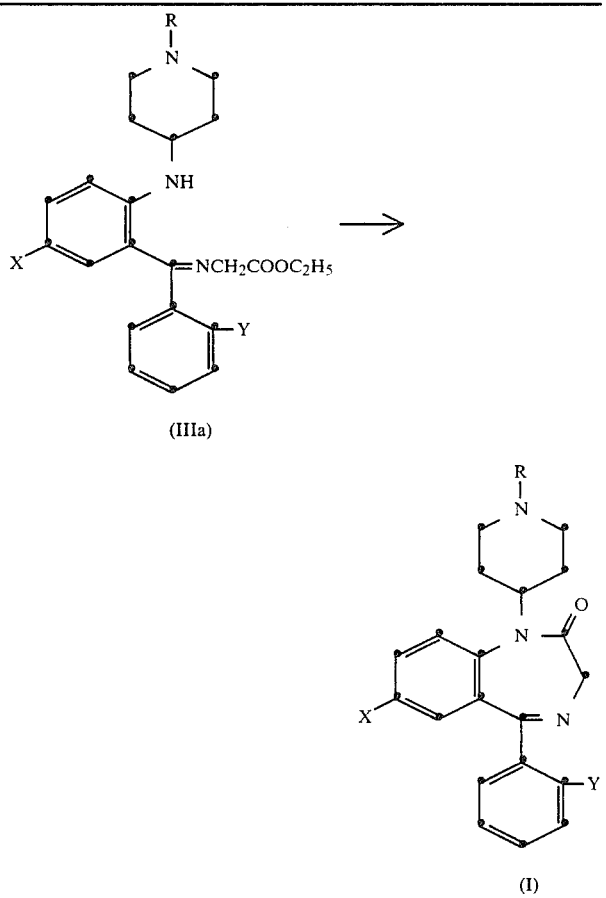

(IIIa)

→

(I)

| Example No. | IIIa | | | | | I | |
|---|---|---|---|---|---|---|---|
| | R | X | Y | Yield (%) | mp (°C.)/ IR(cm$^{-1}$)/ NMR(CDCl$_3$)δ | Yield (%) | mp (°C.) |
| 2 | CH$_3$ | Cl | F | 100 | 3160, 1740 (CHCl$_3$) | 76 | 145–147 |
| 3 | H | H | H | 100 | 3170, 1740 (CHCl$_3$) | 69 | 290–292 (dec.) (HBr) |
| 4 | H | Cl | F | 92 | 123–126 | 61 | 261–262 (dec.) (HBr) |
| 5 | CH$_3$ | Cl | H | 95 | 118–119 | 71 | 242–247 (dec.) (HCl) |
| 6 | CH$_3$ | F | H | 100 | 3160, 1740 (CHCl$_3$) | 84 | 256–258 (dec.) (HCl) |
| 7 | CH$_3$ | F | F | 100 | 3160, 1740 (CHCl$_3$) | 69 | 146–148 |
| 8 | CH$_3$ | Br | H | 100 | 2.3 (3H, s, NC$\underline{H_3}$), 4.0 (2H, s, NC$\underline{H_2}$CO) | 51 | 247–253 (dec.) (HBr) |
| 9 | CH$_3$ | F | Cl | 100 | 3150, 1742 (CHCl$_3$) | 53 | 139–140 |
| 10 | CH$_3$ | Cl | Cl | 100 | 2.3 (3H, s, NCH$_3$) 4.0 (2H, s, NC$\underline{H_2}$CO) | 29 | 146–147 |

EXAMPLE 11

To 6.36 g of ethyl 2-[[[2-(1-methyl-4-piperidinyl-)amino-4-chlorophenyl](2-fluorophenyl)methylen-]amino]acetate is added 32 ml of conc. sulfuric acid under ice cooling, and the resultant mixture is stirred at 95° C. for 13 hours. After cooling the reaction mixture is poured onto 150 g of ice, mixed with a solution of 49 g of sodium hydroxide and 200 ml of water under ice cooling and extracted with benzene. The benzene layer is washed with water, dried over anhydrous magnesium sulfate and concentrated. The residue is crystallized from methylene chloride-ether to give 3.62 g of 7-chloro-5-(2-fluorophenyl)-1-(1-methyl-4-piperidinyl)-1,3-dihydro-1,4-benzodiazepin-2-one as crystals melting at 145° to 146° C. Further 560 mg of the same product is obtained from the mother liquor. The yield is 75%.

EXAMPLE 12

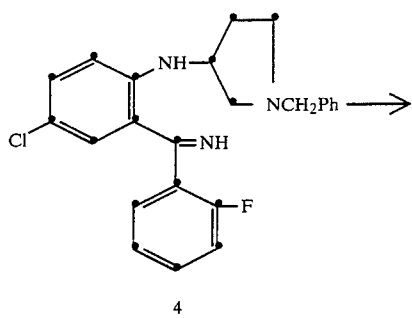

4

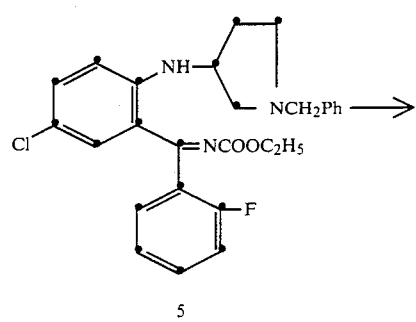

5

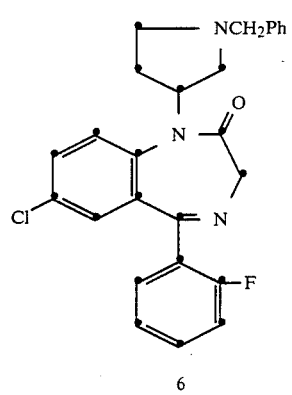

6

The reactions are performed as in Example 1, whereby the following products are obtained.

| Compd. No. | mp (°C.)/ IR (cm$^{-1}$)/ N$^1$NMR (δ) | Yield (%) |
|---|---|---|
| 4 | 3280, 3190 (CHCl$_3$) | 100 |
| 5 | 3170, 1745 (CHCl$_3$) | 100 |
| 6 | 155–156 | 77 |

Example 13

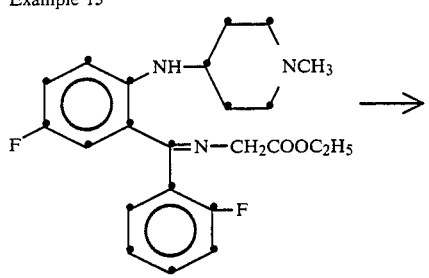

7

| Compd. No. | mp (°C.)/ IR (cm$^{-1}$)/ N$^1$NMR (δ) | Yield (%) |
|---|---|---|
| 8 | | |

A mixture of 50 g of 7 and 250 g of polyphosphoric acid is heated at 100° to 105° C. (bath temperature) for 4 hours under stirring. After cooling, the reaction mixture is mixed with 320 ml of conc. ammonium hydroxide and 500 g of ice and extracted 3 times with methylene chloride. The organic layer is washed with water, dried over anhydrous magnesium sulfate and concentrated. The residue is mixed with 200 ml of ether, and the resulting precipitate is crystallized from methylene chloride-ether to give 34.4 g of 8 as crystals melting at 146° to 148° C. Further 6.4 g of 8 is obtained from the mother liquor in a conventional manner. The yield is 92%.

EXAMPLE 14

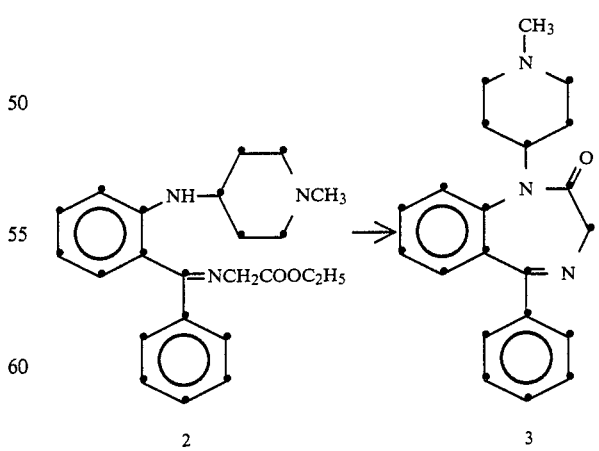

2  3

The reaction is performed in the same manner as in Example 13, whereby 3 is obtained as crystals melting at 158°–159° C. The yield is 79%.

EXAMPLE 15

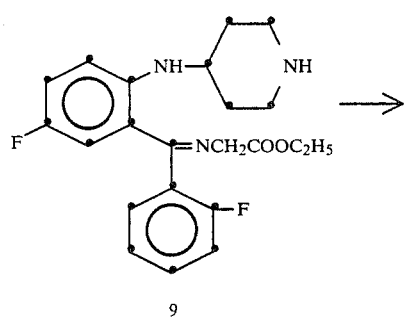

9

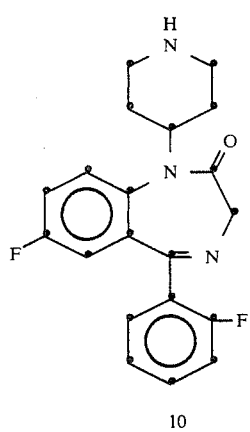

10

A mixture of 3 g of 9 and 30 g of polyphosphoric acid is heated at 100°–105° C. (bath temperature) for 20 hours under stirring. After cooling, the reaction mixture is mixed with ice water and extracted with ether. The acidic layer is alkalized with ice-conc. ammonium hydroxide and the mixture is extracted with methylene chloride. The extract is treated as in Example 13, whereby 1.7 g of 10 is obtained as crystals melting at 150°–151° C. (recrystallized from methylene chloride-ether). The yield is 65%.

REFERENTIAL EXAMPLE 1

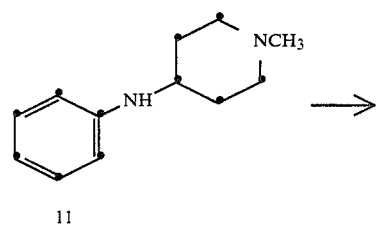

11

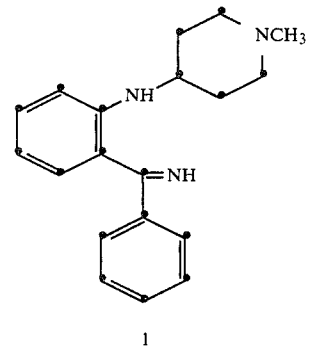

1

To a solution of 5.9 ml (12 mmol) of 2.03M boron trichloride-toluene are added a solution of b 1.90 g (10 mmol) of 4-anilino-1-methylpiperidine 11 in 15 ml of toluene and 2.04 ml (20 mmol) of benzonitrile in that order under ice cooling and stirring, and the resultant mixture is refluxed under stirring for 17 hours. After cooling, the reaction mixture is mixed with 80 ml of methylene chloride and 100 ml of 2N sodium hydroxide in that order and stirred at room temperature for 2 hours. The organic layer is washed with water, dried over anhydrous magnesium sulfate and concentrated under reduced pressure. The residue is crystallized from ethanol to give 2.64 g of 2-(1-methyl-4-piperidinyl)aminobenzophenoneimine 1 as crystals melting at 117° to 118° C. The yield is 90%.

REFERENTIAL EXAMPLE 2-10

The reaction is performed in the same manner as in Referential Example 1, using the following compound (IV), whereby the corresponding compound (II) is prepared.

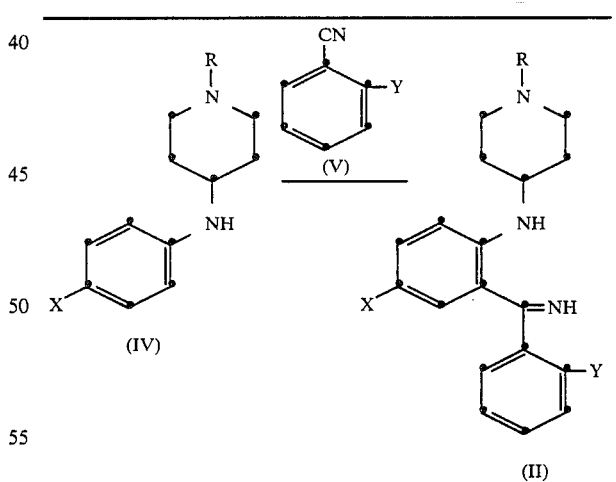

| Ref. Ex. No. | R | X | Y | mp (°C.) IR (cm$^{-1}$) | Yield (%) |
|---|---|---|---|---|---|
| 2 | CH$_3$ | Cl | F | 145–146 | 92 |
| 3 | H | H | H | 3270, 3180, 3055, 1602 (CHCl$_3$) | 100* |
| 4 | H | Cl | F | 3280, 3200, 1605 (CHCl$_3$) | 100* |
| 5 | CH$_3$ | Cl | H | 115–117 | 98 |
| 6 | CH$_3$ | F | H | 130–131 | 87 |
| 7 | CH$_3$ | F | F | 131–132 | 96 |
| 8 | CH$_3$ | Br | H | 110–112 | 85 |

-continued

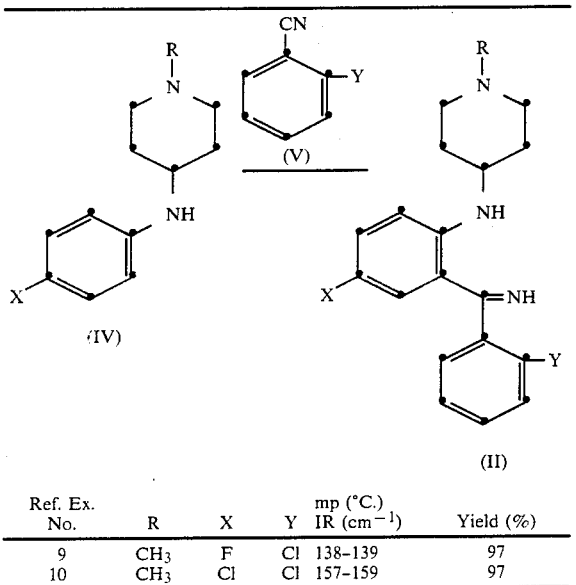

| Ref. Ex. No. | R | X | Y | mp (°C.) IR (cm$^{-1}$) | Yield (%) |
|---|---|---|---|---|---|
| 9 | CH$_3$ | F | Cl | 138–139 | 97 |
| 10 | CH$_3$ | Cl | Cl | 157–159 | 97 |

*Dihydrochloride of IV is used as a starting material.

REFERENTIAL EXAMPLE 11

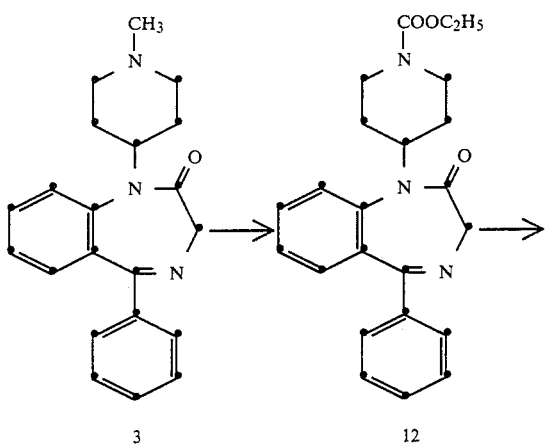

(1) A solution of 98 mg (0.29 mmol) of 1,3-dihydro-1-(1-methyl-4-piperidinyl)-5-phenylbenzodiazepin-2-one 3, 0.084 ml (0.29×3 mmol) of ethyl chloroformate and 54.3 mg (0.29×2.2 mmol) of sodium hydrogencarbonate in 5 ml of benzene is refluxed under heating for 7 hours. The reaction mixture is poured into ice water and extracted with methylene chloride. The organic layer is washed with water dried over anhydrous magnesium sulfate and concentrated to give 114 mg of 1-(1-ethoxycarbonyl-4-piperidinyl)-1,3-dihydro-5-phenyl-2H-1,4-benzodiazepin-2-one 12 as powders. The yield is 100%.

(2) A mixture of 100 mg (0.26 mmol) of the above product 12, 0.5 ml of methyl sulfide and 0.5 ml of methanesulfonic acid is heated at 70° C. for 5 hours. The reaction mixture is mixed with ice, basified with potassium carbonate and extracted with methylene chloride. The organic layer is washed with water, dried over anhydrous magnesium sulfate, and concentrated to give 73 mg of 1,3-dihydro-5-phenyl-1-(4-piperidinyl)-2H-1,4-benzodiazepin-2-one 13 as powders. The yield is 90%.

REFERENTIAL EXAMPLE 12

The reaction of above Referential Example 11 (2) is performed except for using ethyl sulfide in place of methyl sulfide. Refluxing is continued under heating for 5 hours, whereby the same product is obtained as its hydrobromide. m.p. 290° to 292° C. (dec.). The output is 28.2 g. The yield is 75%.

REFERENTIAL EXAMPLE 13

The reaction of above Referential Example 11 (2) is performed except for using ethyl sulfide and sulfuric acid in place of methyl sulfide and methanesulfonic acid. Heating is made at 110° C. under stirring for 1.5 hours, whereby 417 mg of the product is obtained in the form of its hydrobromide. The yield is 74%.

REFERENTIAL EXAMPLE 14–19

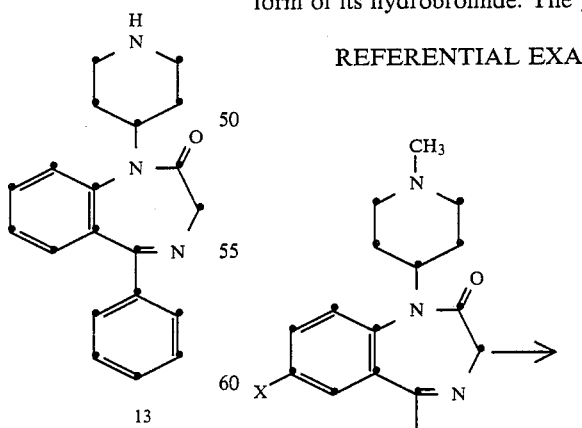

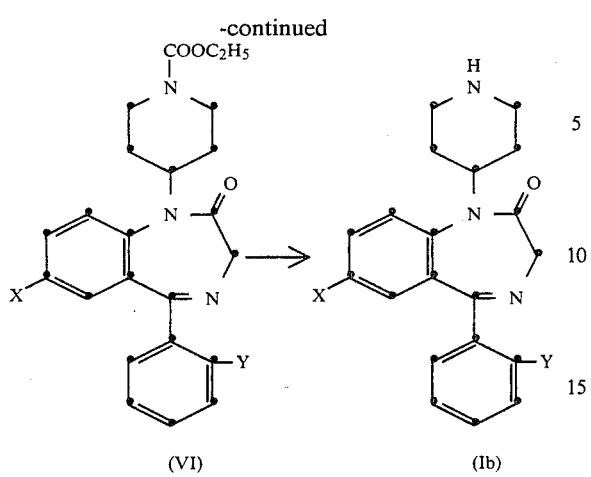

(VI)          (Ib)

The reactions are performed in the same manner as in Referential Example 11, whereby the following compounds (VI) and (Ib) are obtained.

| Ref. Ex. No. | X | Y | VI Yield (%) | VI mp (°C.) ¹HNMR(δ)(CDCl₃) | Ib Yield (%) | Ib mp (°C.) |
|---|---|---|---|---|---|---|
| 14 | F | H | 94 | 3.74, 4.74 (2H, ABq, J = 11Hz COC$\underline{H_2}$N) | 93 | 121–122 |
| 15 | F | F | 95 | 3.76, 4.78 (2H, ABq, J = 11Hz COC$\underline{H_2}$N) | 74 | 150–151 |
| 16 | Cl | F | 84 | 160–161 | 92 | 197–199 (dec) |
| 17 | Br | H | 63 | 3.70, 4.72 (2H, ABq, J = 11Hz COC$\underline{H_2}$N) | 88 | 194–198 |
| 18 | F | Cl | 94 | 3.77, 4.80 (2H, ABq, J = 11Hz, COC$\underline{H_2}$N) | 79 | 276–278 (dec) (HCl) |
| 19 | Br | F | 90 | 3.72, 4.78 (2H, ABq, J = 11Hz COC$\underline{H_2}$N) | 80 | 201–202 |

REFERENTIAL EXAMPLE 20

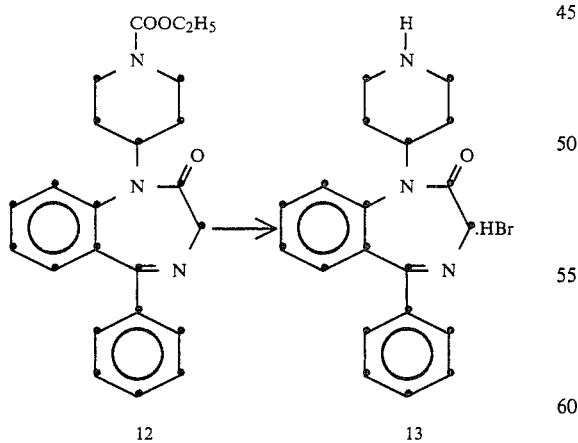

12          13

To a solution of 1 g (2.6 mmol) of 12 in 1.1 ml (2.6×5 mmol) of tetrahydrothiophene is added 2 ml of methanesulfonic acid, and the mixture is heated at 110° C. (bath temperature) for 50 minutes. The reaction mixture is poured into ice water and shaken with ether. The aqueous layer is besified with aqueous potassium carbonate and extracted with methylene chloride. The methylene chloride layer is concentrated, and the residue is dissolved in 1 ml of methanol and mixed with 0.27 ml of 48% hydrobromic acid. The resultant crystals are recrystallized from methylene chloride-methanol to give 881 mg of 13 as crystals melting at 281°–283° C. (dec.). The yield is 86%.

REFERENTIAL EXAMPLE 21

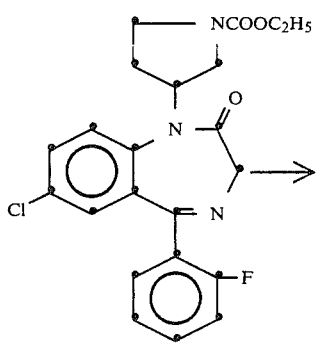

14

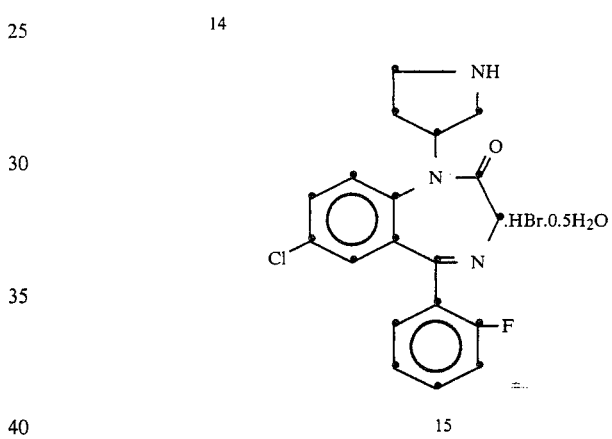

15

The reaction is performed in the same manner as in Referential Example 20, using 14*, whereby 15 is obtained as crystals melting at 220°–221° C. (dec.).

* oil, IR: 1700, 1690 cm⁻¹ (CHCl₃); ¹HNMR: δ$^{(CDCl_3)}$: 3.76, 4.75 (2H, ABq, J=10 Hz, COC$\underline{H_2}$N).

REFERENTIAL EXAMPLE 22

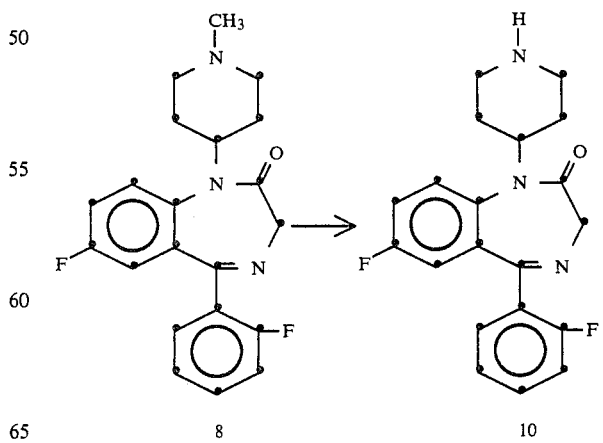

8          10

To a stirred solution of 10 g (27.1 mmol) of 8 in 100 ml of methylene chloride is added a solution 3.88 g (27.1 mmol) of 1-chloroethyl chloroformate* in 20 ml of dichloromethane at −5° C., and the resultant mixture is refluxed for 1 hour. After cooling, the mixture is mixed with 40 ml of methanol, refluxed for 5 hours and concentrated. The residue is mixed with water and basified with 2N sodium hydroxide and extracted with methylene chloride. The organic layer is concentrated and the residue is crystallized from ethyl acetate to give 4.2 g of 10 as crystals melting at 150°–151° C. Moreover 2.3 g of the same product is recovered from the mother liquor. The yield is 68%.

* German Unexamd. Pat. Publn. No. 2,816,873

What we claim is:

1. A process for preparing a compound of the formula:

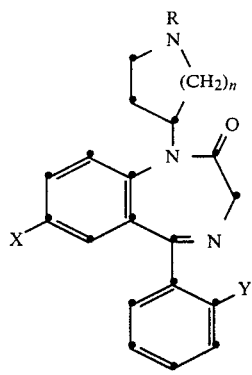

(wherein R is hydrogen, methyl, or benzyl, X and Y are each hydrogen or halogen and n is an integer of 1 to 2) or its acid addition salts which comprises reacting a compound of the formula:

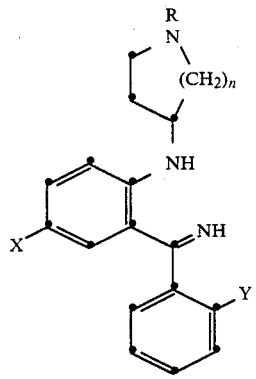

(wherein R, X, Y and n are as defined above) with a glycine ester in a solvent to give a compound of the formula:

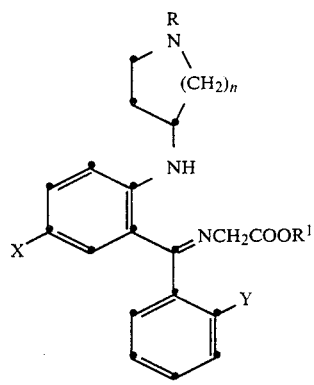

(wherein $R^1$ is $C_1$–$C_5$ alkyl or phenyl-$C_1$–$C_5$ alkyl and R, X, Y and n are as defined above) and treating said product with an acid.

2. A process according to claim 1, in which the acid is selected from the group consisting of acetic acid, sulfuric acid, methanesulfonic acid, p-toluenesulfonic acid, trifluoroacetic acid, trichloroacetic acid, and polyphosphoric acid.

3. The process according to claim 1, wherein the solvent is selected from the group consisting of methanol, ethanol, dimethylformamide, dimethylsulfoxide, and chloroform.

4. The process according to claim 1, wherein the glycine ester is selected from the group consisting of glycine methyl ester, glycine ethyl ester, glycine propyl ester, and glycine benzyl ester.

5. The process according to claim 1, wherein the treatment with the acid occurs at a temperature of about 20° to 150° C.

6. A compound of the formula:

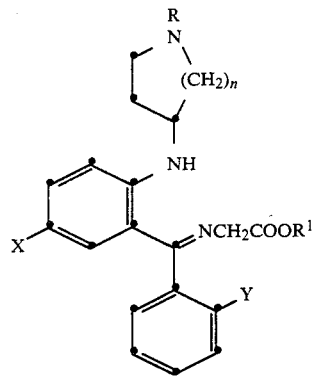

(wherein R is hydrogen or $C_1$–$C_5$ alkyl, $R^1$ is $C_1$–$C_5$ alkyl or phenyl-$C_1$–$C_5$ alkyl, X and Y are each hydrogen or halogen and n is an integer of 1 to 2) or its acid addition salts.

7. A compound according to claim 6, namely ethyl [[[2-(1-methyl-4-piperidinyl)aminophenyl](phenyl)methylen]amino]acetate.

8. A compound according to claim 6, namely ethyl [[[2-(1-methyl-4-piperidinyl)amino-5-chlorophenyl](2-fluorophenyl)methylen]amino]acetate.

9. A compound according to claim 6, namely ethyl [[[2-(4-piperidinyl)aminophenyl](phenyl)methylen]amino]acetate.

10. A compound according to claim 6, namely ethyl [[[2-(4-piepridinyl)amino-5-fluorophenyl](2-fluorophenyl)methylen]amino]acetate.

11. A compound according to claim 6, namely ethyl [[[2-(4-piperidinyl)amino-5-chlorophenyl](2-fluorophenyl)methylen]amino]acetate.

12. A compound according to claim 6, namely ethyl [[[2-(1-methyl-4-piperidinyl)amino-5-chlorophenyl](-phenyl)methylen]amino]acetate.

13. A compound according to claim 6, namely ethyl [[[2-(1-methyl-4-piperidinyl)amino-5-fluorophenyl](-phenyl)methylen]amino]acetate.

14. A compound according to claim 6, namely ethyl [[[2-(1-methyl-4-piperidinyl)amino-5-fluorophenyl](2-fluorophenyl)methylen]amino]acetate.

15. A compound according to claim 6, namely ethyl [[[2-(1-methyl-4-piperidinyl)amino-5-bromophenyl](-phenyl)methylen]amino]acetate.

16. A compound according to claim 6, namely ethyl [[[2-(1-methyl-4-piperidinyl)amino-5-fluorophenyl](2-chlorophenyl)methylen]amino]acetate.

17. A compound according to claim 6, namely ethyl [[[2-(1-methyl-4-piperidinyl)amino-5-chlorophenyl](2-chlorophenyl)methylen]amino]acetate.

18. A compound according to claim 6, namely ethyl [[[2-(1-methyl-4-piperidinyl)amino-5-chlorophenyl](2-fluorophenyl)methylen]amino]acetate.

19. A compound according to claim 6, namely ethyl [[[2-(1-benzyl-3-pyrrolidinyl)amino-5-chlorophenyl](2-fluorophenyl)methylen]amino]acetate.

* * * * *